United States Patent
Shatkin

(10) Patent No.: US 7,108,511 B1
(45) Date of Patent: Sep. 19, 2006

(54) SYSTEM OF DENTAL RESTORATION OF SINGLE STAGE DENTAL IMPLANTS AND LOADING WITH A PREFORMED CROWN RESTORATION

(76) Inventor: Todd E. Shatkin, 89 Bereaford Ct., Williamsville, NY (US) 14221

( * ) Notice: Subject to any disclaimer, the term of this patent is extended or adjusted under 35 U.S.C. 154(b) by 161 days.

(21) Appl. No.: 10/641,797

(22) Filed: Aug. 15, 2003

(51) Int. Cl.
*A61C 8/00* (2006.01)

(52) U.S. Cl. ..................................... 433/174
(58) Field of Classification Search ............... 433/172, 433/173, 174, 175, 176
See application file for complete search history.

(56) References Cited

U.S. PATENT DOCUMENTS

| | | | |
|---|---|---|---|
| 4,318,696 A | 3/1982 | Kasama et al. | |
| 4,693,686 A | 9/1987 | Sendax | |
| 4,702,697 A | 10/1987 | Linkow | |
| 4,975,059 A | 12/1990 | Sendax | |
| 5,246,370 A | 9/1993 | Coatoam | |
| 5,456,601 A | 10/1995 | Sendax | |
| 5,749,732 A | 5/1998 | Sendax | |
| 5,967,783 A * | 10/1999 | Ura ........................... | 433/174 |
| 6,203,324 B1 | 3/2001 | Wils | |
| 6,217,331 B1 | 4/2001 | Rogers et al. | |
| 6,283,753 B1 | 9/2001 | Willoughby | |
| 6,312,260 B1 | 11/2001 | Kumar et al. | |
| 6,358,052 B1 | 3/2002 | Lustig et al. | |
| 6,368,108 B1 | 4/2002 | Locante et al. | |
| 6,394,809 B1 | 5/2002 | Rogers et al. | |
| 6,416,324 B1 | 7/2002 | Day | |
| 2001/0000748 A1 | 5/2001 | Rogers et al. | |
| 2001/0053512 A1 | 12/2001 | Nichinonni | |
| 2002/0004189 A1 | 1/2002 | Hurson | |
| 2002/0039718 A1 * | 4/2002 | Kwan ........................ | 433/173 |
| 2002/0064758 A1 | 5/2002 | Lee | |
| 2002/0090592 A1 | 7/2002 | Riley et al. | |
| 2002/0102516 A1 | 8/2002 | Srouji et al. | |
| 2002/0137003 A1 * | 9/2002 | Knapp ........................ | 433/76 |
| 2002/0142266 A1 | 10/2002 | Rogers et al. | |
| 2002/0150862 A1 | 10/2002 | Day | |
| 2002/0168613 A1 * | 11/2002 | Riley et al. ................. | 433/173 |
| 2003/0031981 A1 | 2/2003 | Holt | |
| 2003/0068599 A1 | 4/2003 | Balfour et al. | |
| 2003/0087217 A1 | 5/2003 | Coatoam | |
| 2003/0232308 A1 * | 12/2003 | Simmons .................... | 433/173 |
| 2005/0181331 A1 * | 8/2005 | Lustig et al. ............... | 433/173 |

* cited by examiner

*Primary Examiner*—Cary E. O'Connor
(74) *Attorney, Agent, or Firm*—Simpson & Simpson, PLLC

(57) ABSTRACT

The present invention is prosthetic tooth replacement including a dental crown portion and a joining portion adapted to fixedly attach to a dental implant. Further, present invention also comprises the combination of a prosthetic tooth replacement and a dental implant. Additionally, the present includes a method for making an oral surgical guide stint by vacuum forming a thermoplastic material over a model of an implant target area. Finally, the present invention includes a method of inserting the combination of the prosthetic tooth replacement and implant into the jaw of a patient.

18 Claims, 11 Drawing Sheets

SYSTEM OF DENTAL RESTORATION OF SINGLE STAGE DENTAL IMPLANTS AND LOADING WITH A PREFORMED CROWN RESTORATION

FIELD OF THE INVENTION

The present invention relates to the field of oral prostheses. More specifically, the present invention relates to the field of dental implants and attached dental crown prostheses. In addition, the present invention relates to oral surgical procedures, more specifically, to surgical procedures enabling the secure attachment of dental crown prostheses in one surgical session in which patient discomfort is reduced.

BACKGROUND OF THE INVENTION

Dental implants are well known devices used in dental surgery to restore patients' lost, broken or decayed teeth. The essential function of a dental implant is to act as an anchor to hold in place a prosthetic device such as a fixed or removable denture appliance or single prosthetic tooth. Implants attain stability by being embedded in the patient's jawbone, thereby giving a firm foundation to the prosthetic device that protrudes above a patient's gum line.

Implants seen in the prior art have several disadvantages. First, to bring an implant procedure to completion requires several patient visits. Usually five to seven or more visits are necessary as well as possible referrals to specialists. The implant procedure itself requires surgery with flap and sutures leading to both significant patient discomfort, temporary restrictions on the types of food patients are permitted to eat, and a four to twelve month time period before the entire procedure is completed. In addition, there is a 10–15% failure rate. Failure of the procedure requires the use of alternative procedures over and above the failed implant surgery. Finally, the complete implant procedure, including the prosthetic device, can entail a high cost often out of the range of the average patient.

Typical of implants found in the prior art are those disclosed in U.S. Pat. Nos. 6,217,331 and 6,394,809 as well as United States Patent Application No. 2002/0142266, all to Rogers, et al. This series discloses a dental implant supporting a single prosthetic crown. The implant is described as having a threaded portion with a self-tapping region which allows insertion into the jawbone of a patient. The gingival portion is flared with a threaded bore that accepts a prosthetic device that extends above the gum line. The size of these implants mandate a waiting period of approximately 3–6 months before the prosthetic device is installed after the implant is first placed into the patient's jaw. This hold period allows ossification of the bone material around the inserted implant to ensure it is sufficiently secured in the bone structure. During this time, a flap is sewn over the implant to prevent infection during the ossification process. The required hold period delays the final installation of the dental prosthesis while the surgery can contribute to significant patient discomfort.

A similar implant is disclosed in United States Patent Application No. 2003/0068599 to Balfour, et al. The implant disclosed in the '599 application includes scalloped buccal and lingual portions that allow for tissue attachment to create a natural appearing gum line. However, the size of the implant disclosed in the '599 application necessitates the use of an insertion procedure that incorporates an extended waiting period to ensure sufficient ossification around the implant occurs.

Vigolo, et al. discloses the use of implants having a diameter in the range of 2.9 mm as supports for prosthetic crowns. [See *The Journal of Prosthetic Dentistry*, 84(1): 50–54 (July 2000) which is hereby incorporated by reference in its entirety.] However, use of implants of this size still require a two month waiting period before a prosthesis can be attached to the implant. Similarly, U.S. Pat. No. 4,313,696 to Kasama, et al., which is hereby incorporated by reference in its entirety, discloses an implant supporting a single prosthetic crown. However, the '696 patent discloses that a period of wound healing must occur after the implant is placed in a patient's jaw. In addition, the device disclosed in the '696 patent includes an elastomeric cushion placed between the prosthetic crown and the implant.

The use of mini dental implants (MDIs) has been disclosed in U.S. Pat. No. 5,749,732 to Sendax, which patent is hereby incorporated by reference in its entirety. The '732 patent discloses an implant having a length of in the range of 17–19 mm, a threaded shaft diameter of about 1.8 mm with the threaded area having an unthreaded chord shaped section. Integral in the MDI of the '732 patent is an abutment end to which a dental prosthesis can be attached. The '732 patent discloses the use of the MDI to anchor a denture appliance holding a plurality of prosthetic teeth and requiring either a second MDI or another anchor such as a natural tooth to hold the denture. Also disclosed in the '732 patent is an implantation procedure for the MDI that eliminates the need for a surgical incision, flap and sutures, and the consequent ossification period before installing the dental prosthesis. However, the advantage of MDIs in enabling fast, relatively pain free insertion of dental prostheses is somewhat negated by their confinement to use with dentures supporting a plurality of artificial crowns and the need to use at least two anchors to support the denture.

Therefore, there exists in the field a need for a dental implant that can be used to securely support single dental crown prosthesis and that can be secured in a patient's jawbone using a procedure that reduces the time to complete installation of the prosthesis and patient discomfort and pain.

SUMMARY OF THE INVENTION

The present invention broadly comprises a preformed prosthetic tooth comprising a dental crown portion and a joining portion that is adapted to fixedly attach to a dental implant. The joining portion is configured to receive the abutment end of a mini dental implant (MDI). The dental crown portion may be formed into the shape of a particular tooth.

The present invention also broadly comprises, in combination, a prosthetic tooth and at least one dental implant having a preformed prosthetic tooth with a dental crown portion and a joining portion that is adapted to fixedly attach to a dental implant. In a preferred embodiment, the dental implant will be a mini dental implant having an integral abutment end.

The present invention also broadly comprises a method of forming a surgical guide stint comprising taking an impression of the target area and opposing jaw area, pouring a model of the bite impression, placing at least one implant analog into position in the model and vacuum forming a stint over the model.

The present invention also broadly comprises a method of attaching a preformed prosthetic tooth to a jawbone of a patient comprising placing an oral surgical stint over a target region of a jawbone, drilling at least one hole having a first diameter into the jawbone through at least one implant analog hole in the oral surgical stint, threading a threaded dental implant having a larger second diameter and an integral abutment end into each drilled hole until only the abutment end protrudes above the gum line of the jawbone and attaching a single prosthetic crown onto the at least one abutment end.

A general object of the invention is to provide a nonsurgical procedure that enables the attachment of a prosthetic crown to the jawbone of a patient.

A second object of the invention is to provide a prosthetic crown securely attached to a self-tapping dental implant.

An additional object of the invention is to provide a preformed prosthetic crown able to be fixedly attached to a dental implant without attachment to an intermediate material.

A further object of the invention is to provide a surgical guide stint to guide the installation of a dental implant into the desired position on a patient's jaw.

BRIEF DESCRIPTION OF THE SEVERAL VIEWS OF THE DRAWINGS

The nature and mode of the operation of the present invention will now be more fully described in the following detailed description of the invention taken with the accompanying drawing Figures, in which:

FIG. 4b is a cross section of the molar-shaped crown portion depicted in FIG. 4a;

FIG. 5b is cross section of a magnified view of the receiving tube and implant abutment end of the present invention shown in FIG. 5a;

DETAILED DESCRIPTION OF THE INVENTION

At the outset, it should be appreciated that like drawing numbers on different drawing views identify identical structural elements of the invention. It also should be appreciated that figure proportions and angles are not always to scale in order to clearly portray the attributes of the present invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Figure 1:
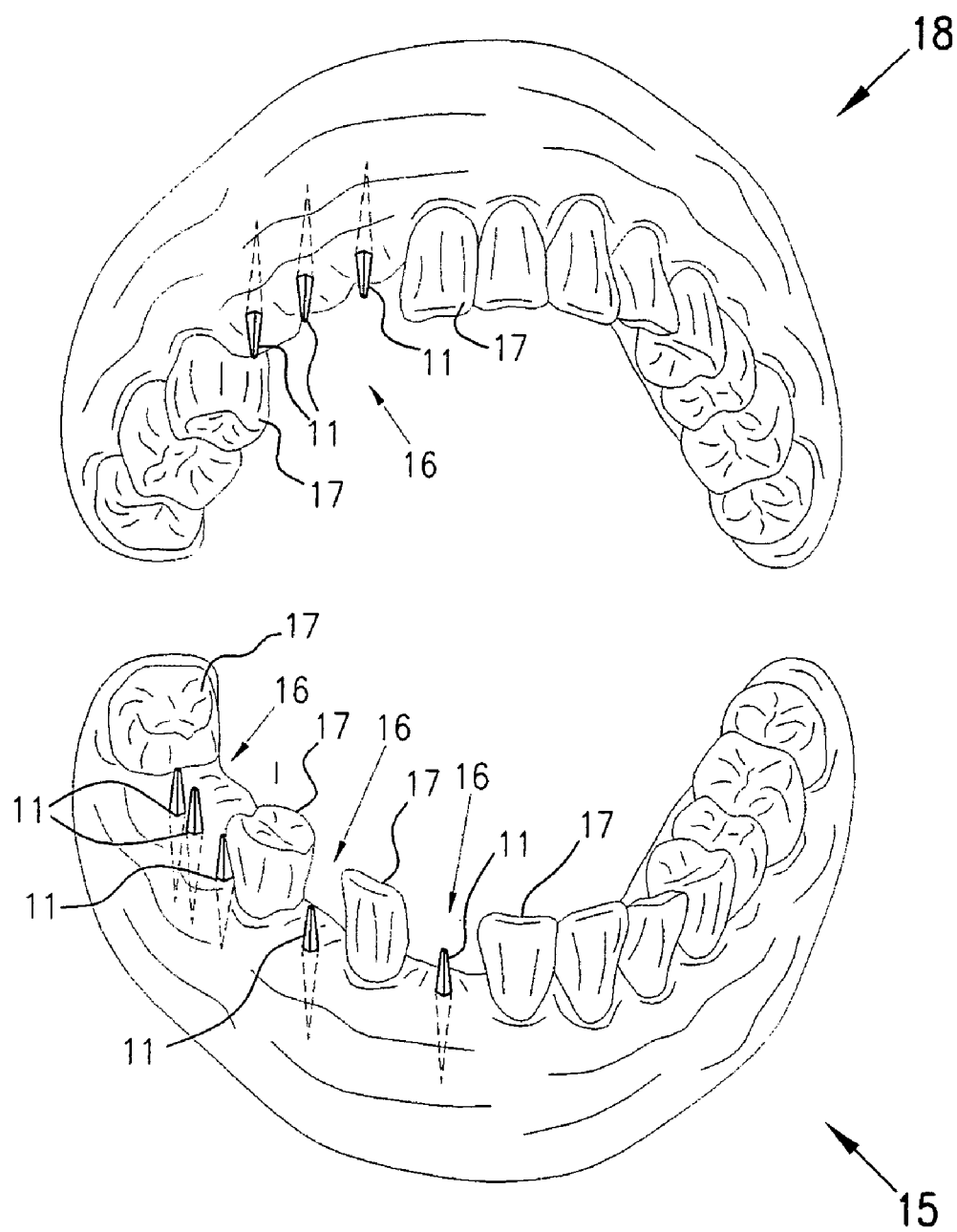
FIG. 1 is a front view of both upper and lower jaws of a human mouth containing implants of the present invention.

Adverting to the drawings, FIG. 1 is a front view of lower jaw 15 and upper jaw 18, each supporting implants 11 of the present invention. Implants 11 are inserted into the bone material of lower jaw 15 and/or upper jaw 18 in gap 16 between teeth 17. Implants may also be inserted in gaps 16 which are not flanked by teeth 17. Gap 16 may be of varying size providing there is sufficient space to contain a preformed crown 21 (not shown in FIG. 1.

Figure 2:
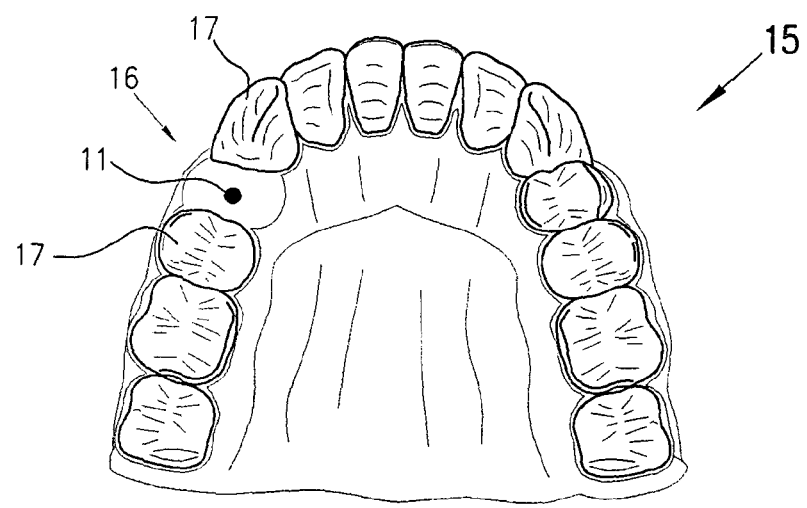
FIG. 2 is a top view of a lower jaw depicting a gap suitable for placement of the dental implant and upper crown of the present invention.
Figures 3A, 3B, 3C:
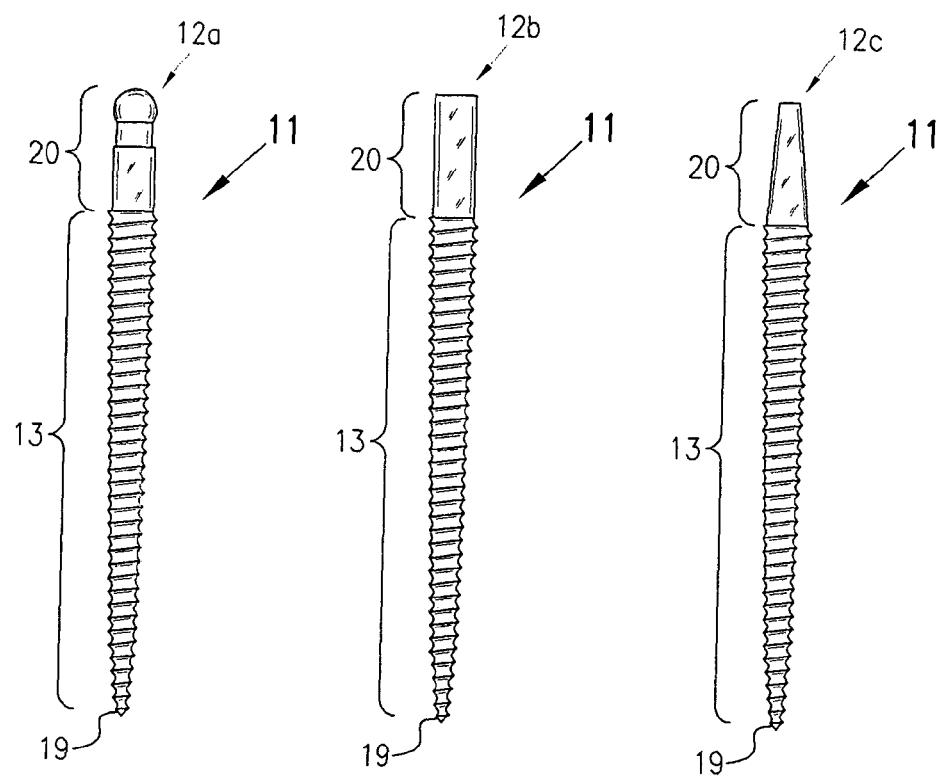
FIGS. 3a–3c are front views of various embodiments of the implant of the present invention.

FIG. 2 is a top view of teeth 17 of lower jaw 15. Implant 11 is found in gap 16 among teeth 17. It should be understood that implant 11 may be located between any teeth of either upper jaw 18 (not seen in FIG. 2) or lower jaw 15. In addition, placement of implant 11 is not restricted to a gap 16 created by a single missing tooth 17. Implants 11 may be placed any area where one or more teeth are missing. FIGS. 3a, 3b, and 3c are side views of several embodiments of implant 11. Implant 11 is a shaft ranging in diameter from 1.6 to 2.5 mm. A more preferred diameter is 1.8–2.2 mm depending on the density of the bone material that will support implant 11. Threaded section 13 extends from tip 19 to carrier section 20. Tip 19 has a point sufficient to enable implant 11 to be self-tapping when it is inserted into lower jawbone 15 or upper jawbone 18. Carrier section 20 is configured in such a way as to allow instruments such as suitably sized wrenches, ratchets, or similar tools to grab and turn implant 11 in order to screw implant 11 into bone material. Abutment end 12 is at the opposite end of implant 11 from tip 19. Abutment end 12 is configured to be inserted into crown 21 (not shown in FIGS. 3a–c.) Abutment end 12 may have any shape including a spherical abutment end 12a as seen in FIG. 3a, a square or rectangular solid abutment end 12b as seen in FIG. 3b, or a polygonal tapered end, such as a pyramidal shaped abutment end 12c, one side of which is seen in FIG. 3c. Other embodiments of abutment end 12 can include a cone configuration and multisided (polygonal) configurations. Any shape of abutment end 12 should be such as to enable insertion into receiving tube 24 of crown 21 as seen below.

Figure 4A:
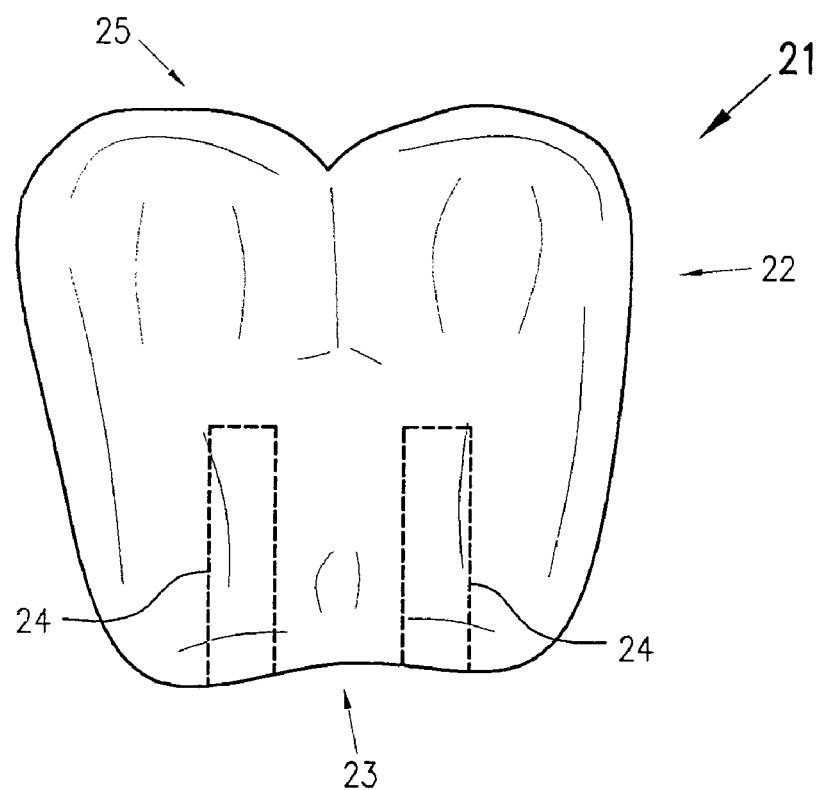
FIG. 4a is side view of a molar-shaped dental crown portion of the present invention.
Figure 4B:
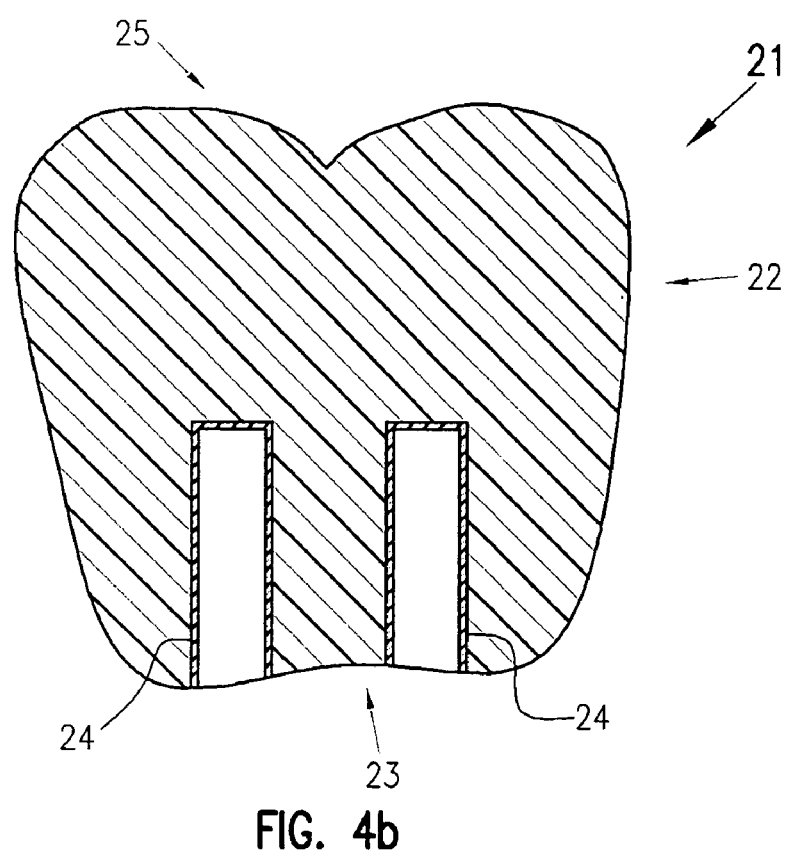
Figure 4C:
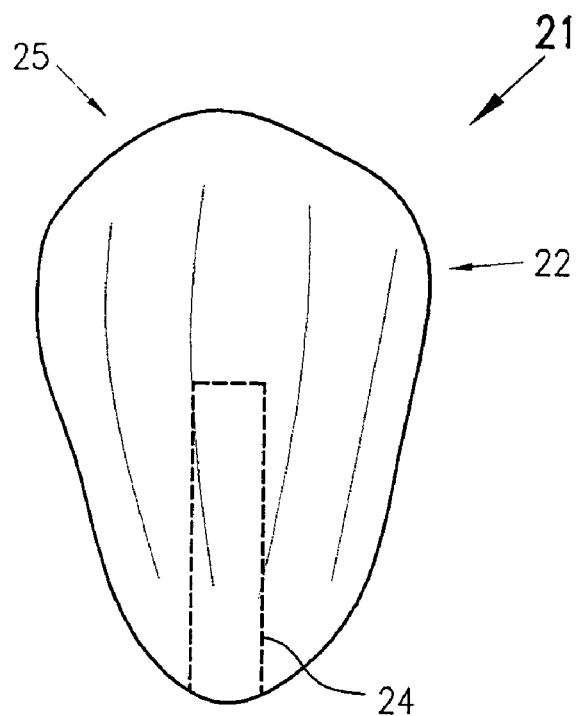
FIG. 4c is a side view of an incisor-shaped crown portion of the present invention.
Figure 4D:
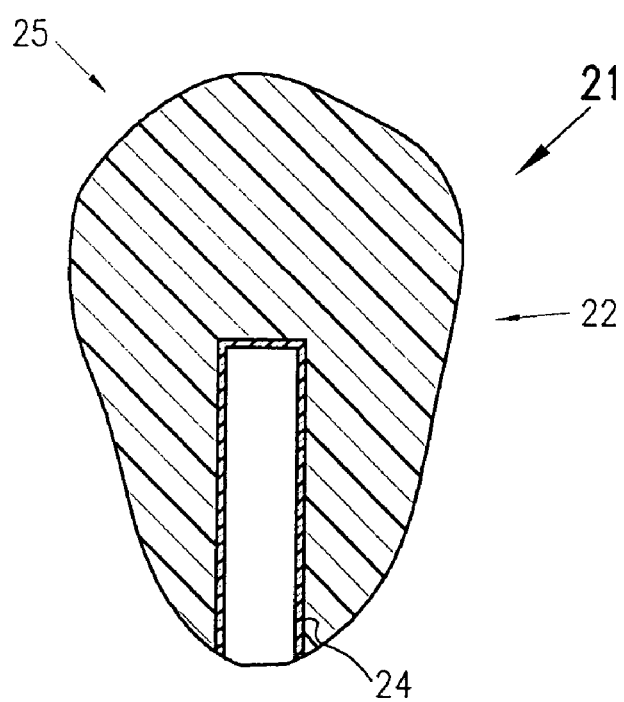
FIG. 4d is a cross section of the incisor shaped crown portion depicted in FIG. 4c.

FIGS. 4a–d depict various views of crown 21. Upper portion 22 of crown 21 may be fabricated from any material used in the manufacture of tooth prostheses. Preferably, suitable resins, porcelain, or a porcelain fused to metal (PFM) combination, all of which are well known to persons of ordinary skill in the art, may be used for forming the upper portion 22. Methods of fabrication of upper portion 22 of crown 21 are well known to those of ordinary skill in the art. Joining portion 23 is located at that part of crown 21 that will contact implant 11 and the gum line (base) of space 16. Joining portion 23 also comprises cavity 24 bored or drilled into upper portion 22 of crown 21. In a preferred embodiment, cavity 24 is a tube with a closed end. Tube 24 is sized to be larger than abutment end 12 so that it may contain not only abutment end 12 but also dental cement 26 that securely holds implant 11 to crown 21. Although dual cured cements are preferred, other dental cements known to those having ordinary skill in the art maybe used. FIGS. 4a and 4b depict a side view and cross section view, respectively of a molar crown 21. Tube 24 of joining portion 23 must be of sufficient length to provide secure support to crown 21 after implant 11 is attached to crown 21. Preferably, tube 24 of joining portion 23 extends to about half of the length of crown 21 as measured from joining portion 23 to top 25 of crown 21. It can be seen that in a preferred embodiment, molar shaped crowns 21, as seen in FIGS. 5a and 5b have two or more tubes 24, while crowns 21 shaped as incisors, bicuspids, and/or cuspids may have one tube 24.

Figure 5A:
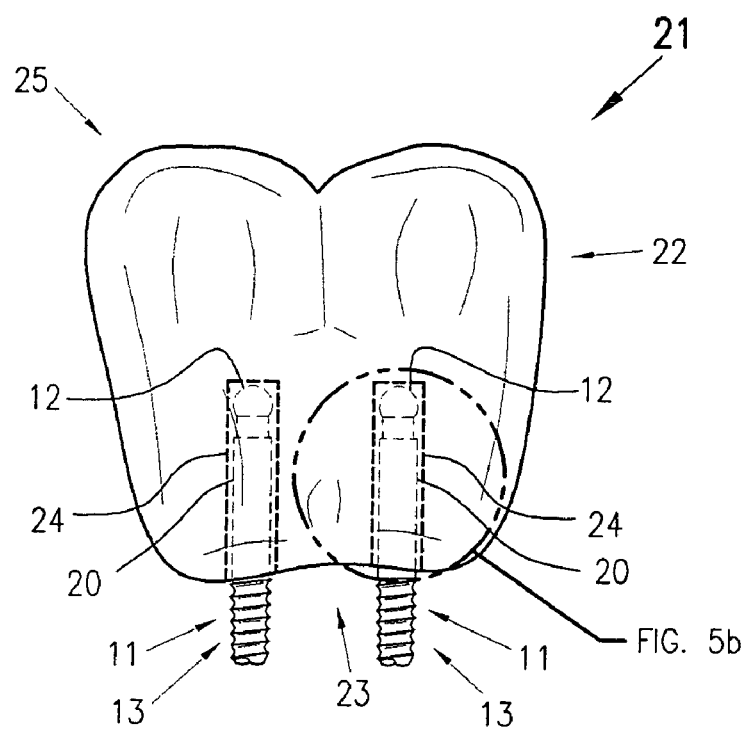
FIG. 5a is a side view of a molar-shaped crown portion of the present invention showing attachment to an implant of the present invention.
Figure 5B:
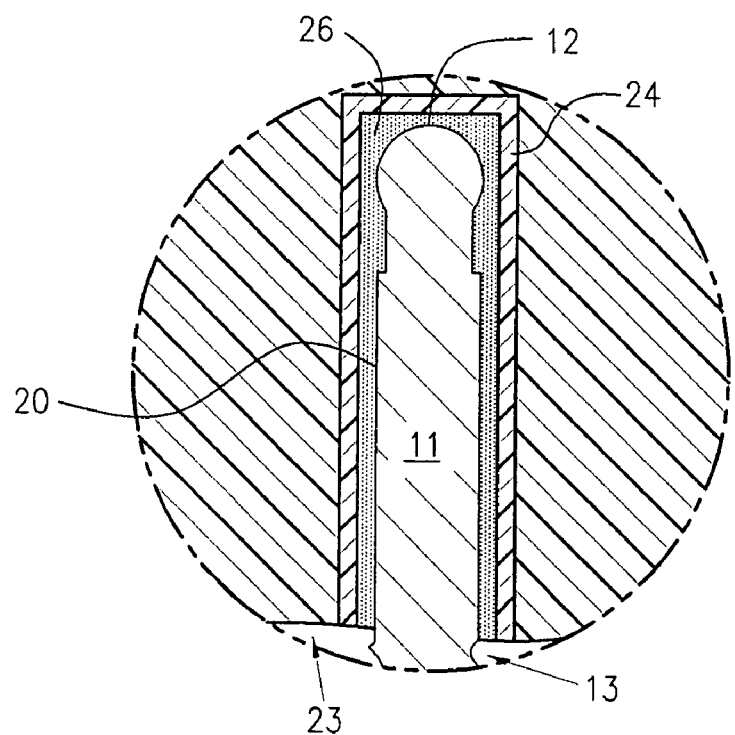
Figure 5C:
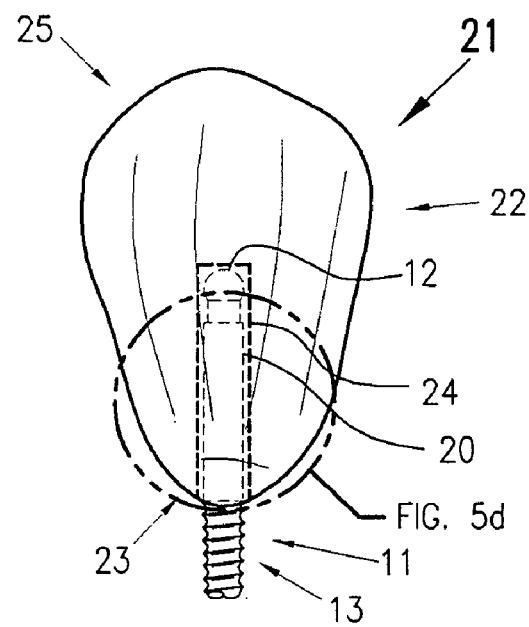
FIG. 5c is a side view of an incisor-shaped crown portion of the present invention showing attachment to an implant of the present invention.
Figure 5D:
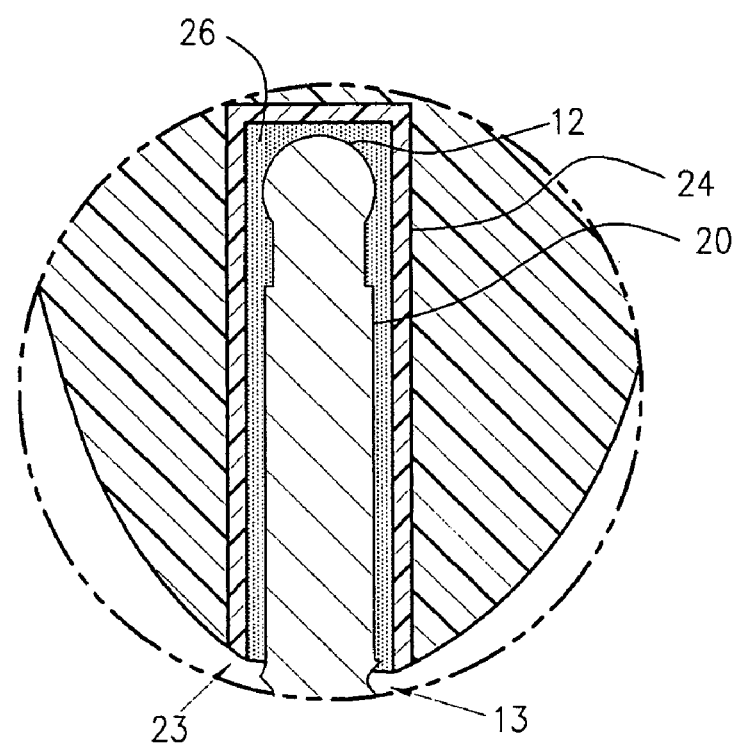
FIG. 5d is cross section of a magnified view of the receiving tube and implant abutment end of the present invention shown in FIG. 5c.

FIGS. 5a through 5d depict crown 21 joined to implant 11 to form the combination prosthesis of the present invention that is fitted into lower jawbone 15 and or upper jawbone 18. Tube 24 is filled with dental cement 26. Implant 11 is then inserted into tube 24 such that abutment end 12 contacts or almost contacts the closed end of tube 24. Excess dental cement 26 is removed. FIG. 5a depicts as shadow implants 11 inserted into tubes 24 of molar crown 21. As mentioned above, molar crown 21, because of the greater surface area of joining portion 23 relatively to nonmolar crowns 21, preferably comprises at least two tubes 24 to receive two implants 11 to ensure molar crown 21 is securely attached to bone material. FIG. 5b depicts the circled area of FIG. 5a showing in greater detail the joining of abutment end 12 with crown 21. Abutment end 12 reaches to the closed end of tube 24 and is surrounded by dental cement 26 which was previously placed into tube 24. In a preferred embodiment, threaded section 13 of implant 11 is embedded entirely below the gum line after being threaded into the bone material. FIG. 5c depicts a nonmolar crown 21, such as an incisor, bicuspid, or cuspid, joined to implant 11. In the preferred embodiment shown, one implant 11 is combined with nonmolar crown 21 to form the combination prosthesis of the present invention. FIG. 5d depicts the circled area of FIG. 5c showing in greater detail the joining of abutment end 12 with crown 21. Abutment end 12 reaches to the closed end of tube 24 and is surrounded by dental cement 26 which was previously placed into tube 24. In a preferred embodiment, threaded section 13 of implant 11 is embedded entirely below the gum line after being threaded into the bone material. To correctly position the dental prosthesis of the present invention on a patient's jaw, an impression is made of the area that will receive the prosthesis. The impression should be of the type to include not only the receiving area but also the region opposite the receiving area. By "opposite" is meant the region directly located above or below the receiving area on the opposite jaw bone. Typical impressions can be a triple tray impression or full arch impressions with full bite registration. Such impressions are well known to those skilled in the art.

Figure 6:
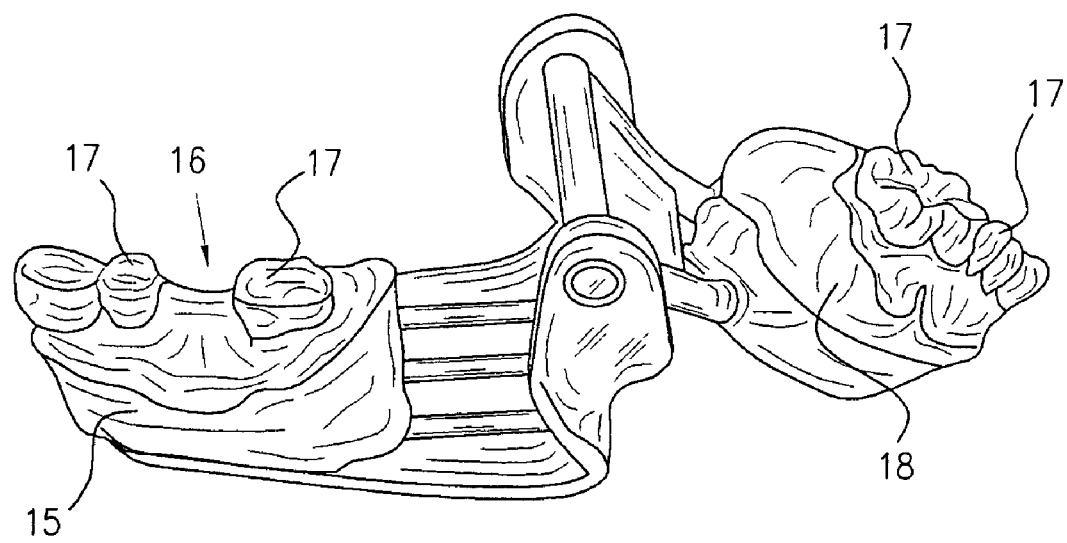
FIG. 6 depicts attached models of lower and upper jaws fabricated from impressions taken from a typical patient.
Figure 6A:
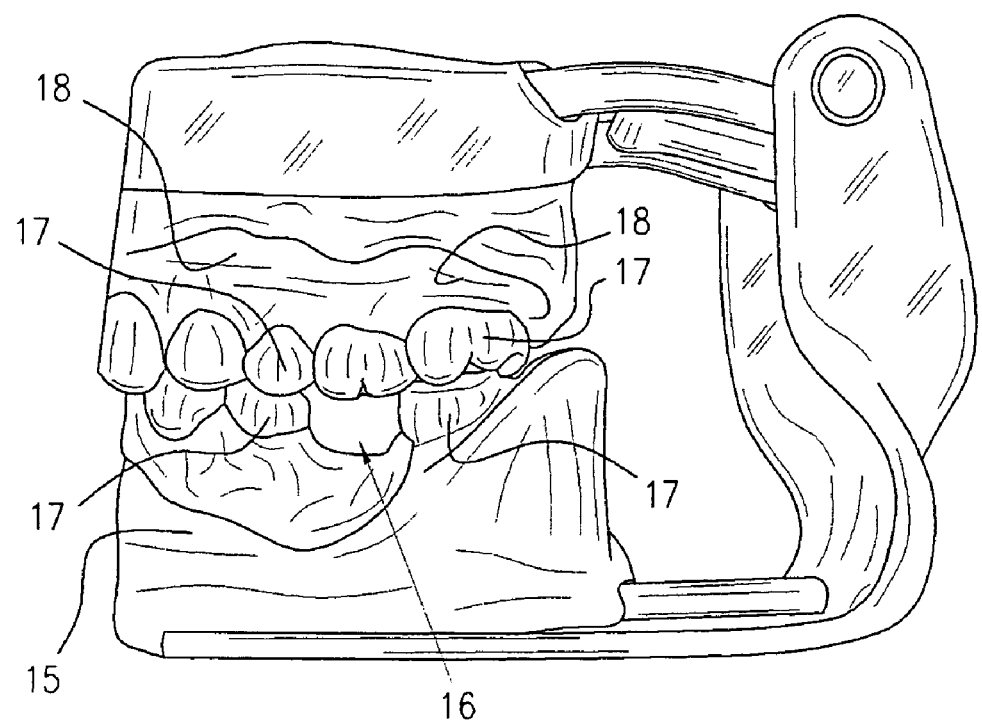
FIG. 6a depicts the lower and upper jaw models shown in FIG. 6 in a closed position.

FIGS. 6 and 6a depict a model created from an impression (s) made of both the target area, gap 16, in lower jaw 15 and the region on upper jaw 18 directly opposing gap 16. The fabrication of such models are well known to those skilled in the art. The opposing region is used as an aid to determine the alignment of the prosthesis in relation to the gum line of jaw 15 and proper bite occlusion.

Figure 7:
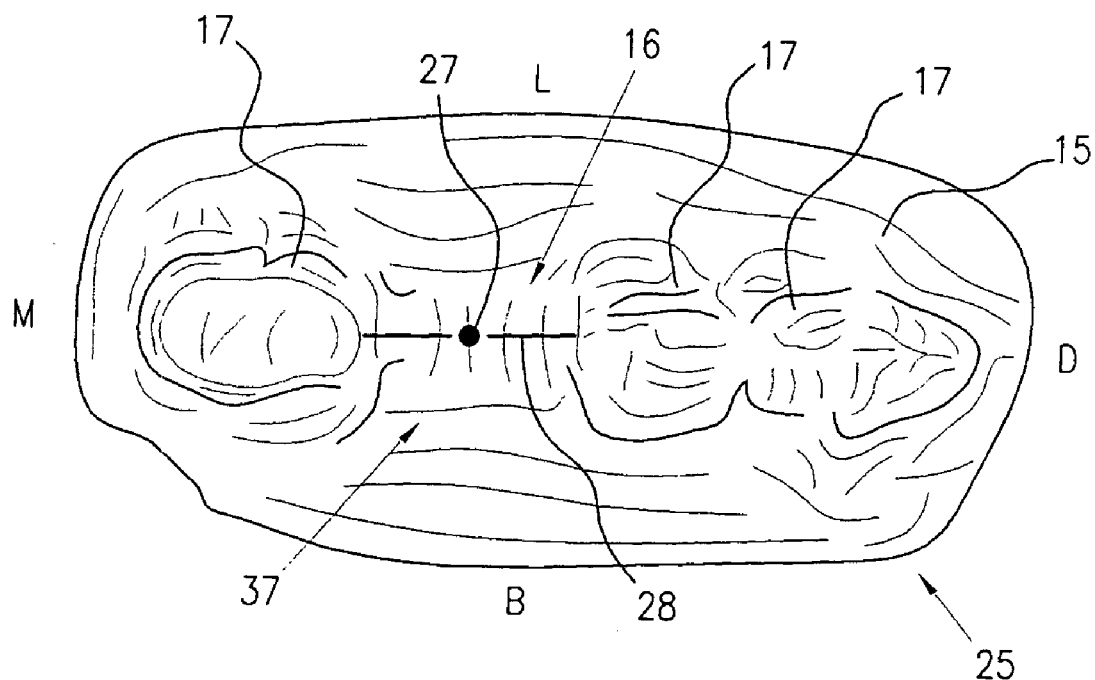
FIG. 7 is a top view of a model of a lower jaw depicting the position of a single implant hole.

FIG. 7 is a top view of gap 16 of lower jaw 15. To determine the position 27 of single implant 11, the center of the dental ridge 26 is located on model 25. A single implant 11 is placed on the center of dental ridge 37 equidistant between the mesial (front) side, labeled M, and distal (back) side, labeled D, of gap 16.

Figure 7A:
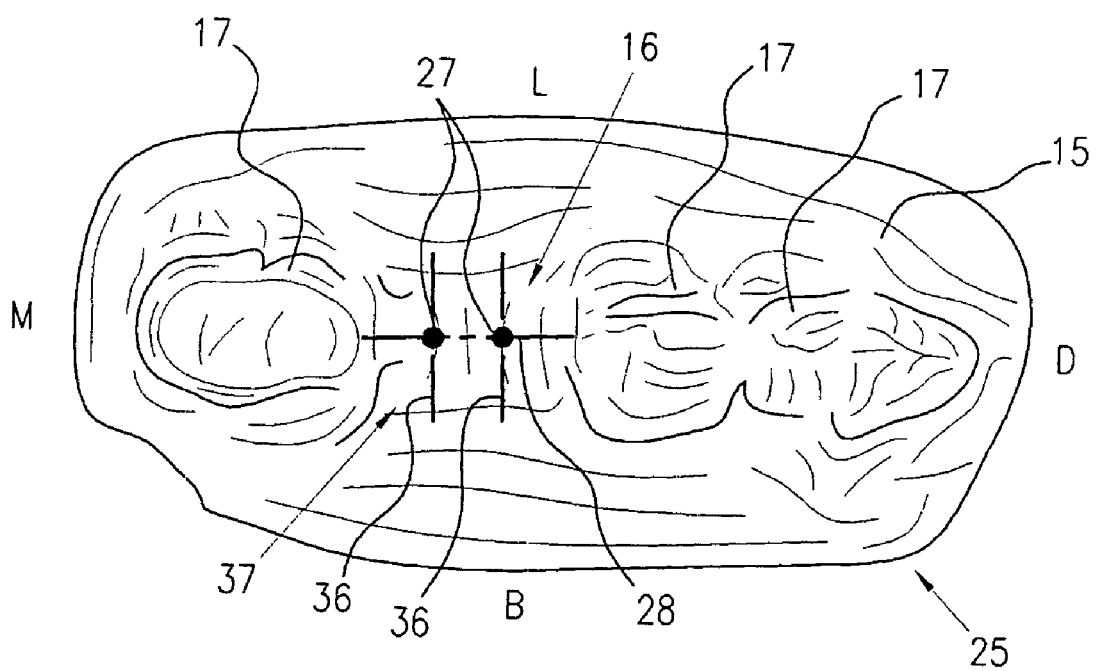
FIG. 7a is a top view of a model of a lower jaw depicting the position of two implant holes.

FIG. 7a depicts the positions 27 of gap 16 in which two implants 11 are located. As mentioned above, in a preferred embodiment, at least two implants 11 are used to hold a molar crown 21. Again, the position of the centerline 28 of dental ridge 37 is ascertained. Gap 16 is divided into thirds along the mesial-distal axis to enable implants 11 to be placed equidistant from the mesial and distal ends of gap 16 as well as equidistant from each other. A preferred method of determining the implant position is to divide gap 16 into three equal sized sections using cross-lines 36 and then placing implants 11 at the point 27 where cross lines 36 intersect the center line 28 of dental ridge 26.

The angle of the tapping hole for implant 11 is found by determining that angle which will maintain an equal quantity of bone material on both the buccal (B) and lingual side (L) of the implant hole 29. Using this method, implant(s) 11 are positioned so as to absorb equal amounts of pressure and wear from all sides of gap 16.

Figure 8:
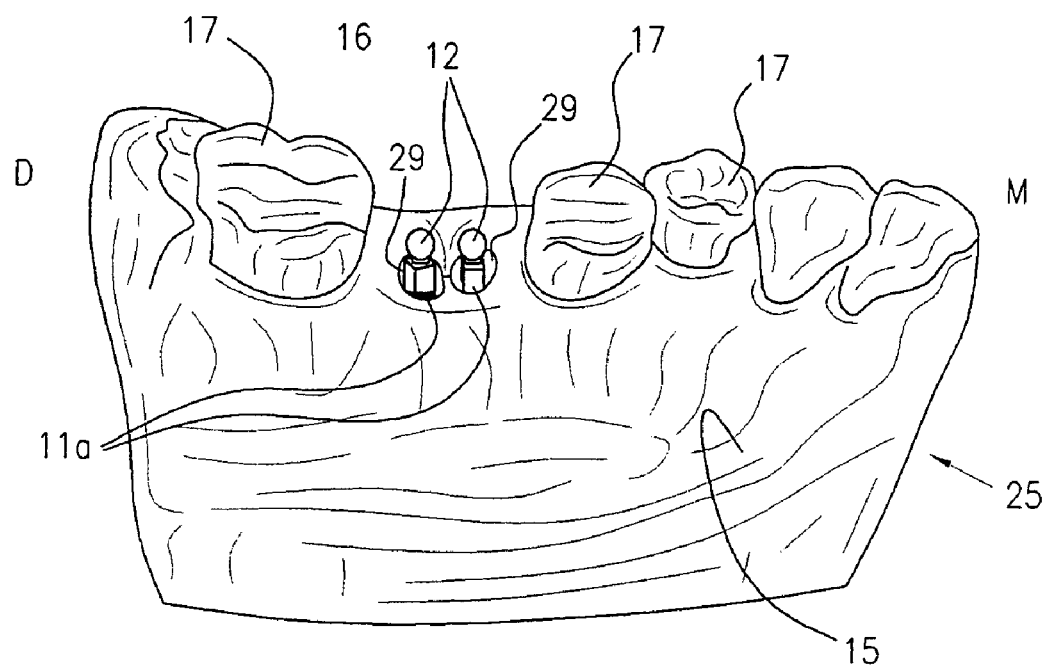
FIG. 8 is a side perspective view of a model of a lower jaw showing implant analogs placed in implant analog holes.
Figure 9:
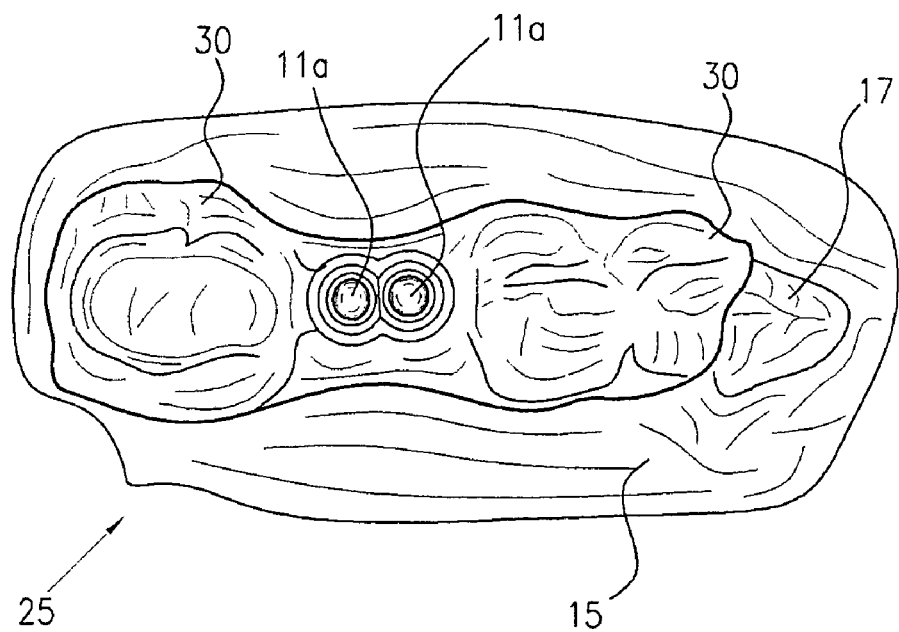
FIG. 9 is a top view of a model of a lower jaw showing a stint placed in position around implant analogs.
Figure 10:
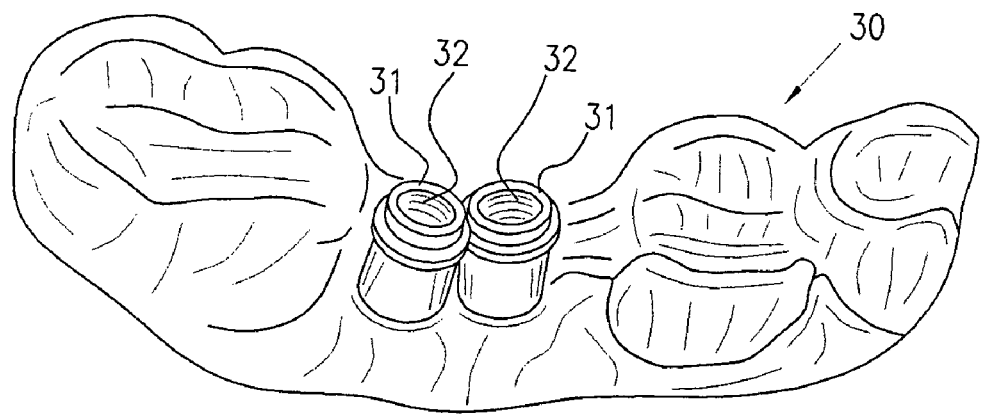
FIG. 10 is a top perspective view of an oral surgery guide stint of the present invention.

As seen in FIG. 8, implant orifices or hole(s) 29 are drilled or bored into model 25 and implant analog(s) 11a are placed into hole(s) 29. Implant analogs 11a have abutment ends 12 and carrier sections 20 similar in size to actual implants, but they may lack threaded section 13 as there is no need to tap into model 25. As seen in FIG. 9, stint 30 is then placed over gap 16 so as to rest on teeth 17 on either side of gap 16. Stint 30 is made from any suitable thermoplastic material capable of vacuum forming over model 25. The vacuum process acts to mold stint 30 into the shape of the implant receiving area comprising gap 16, implant analog(s) 11a, and surrounding teeth 17. In a preferred embodiment of the stint forming procedure, cylinders 31 are placed around implant analogs 11a and into hole(s) 29 so that the cylindrical wall of cylinder(s) 31 surrounds the shaft of implant analog(s) 11a with abutment end 12 of implant analog 11a remaining uncovered. With cylinder(s) 31 in place, the vacuum forming process incorporates cylinder(s) 31 into molded stint 30 creating guide hole(s) 32 as part of molded stint 30. FIG. 10 is a top perspective view of stint 30 with incorporated guide hole(s) 32 which is molded to the shape of the area of a patient's jaw where implant(s) 11 are to be placed.

To insert implant(s) 11 into lower jaw 15 or upper jaw 18, molded stint 30 is placed over gap 16 where implant(s) 11 are to be inserted. As a result of the vacuum forming process described above, the configuration of molded stint 30 enables it to fit or overlay snugly on adjacent teeth 17 on the mesial and distal sides of gap 16 as well as on the surface of gap 16. Again, as a result of the vacuum forming process, guide hole(s) 32 are positioned within gap 16 at the predetermined location(s) analogous to the positions of implant analog(s) 11a in model 25. Moreover, in the preferred embodiment, the incorporation of cylinder(s) 31 into stint 30 orients guide hole(s) 32 into the desired angle for inserting implant(s) 11 into the bone material.

Figure 11:
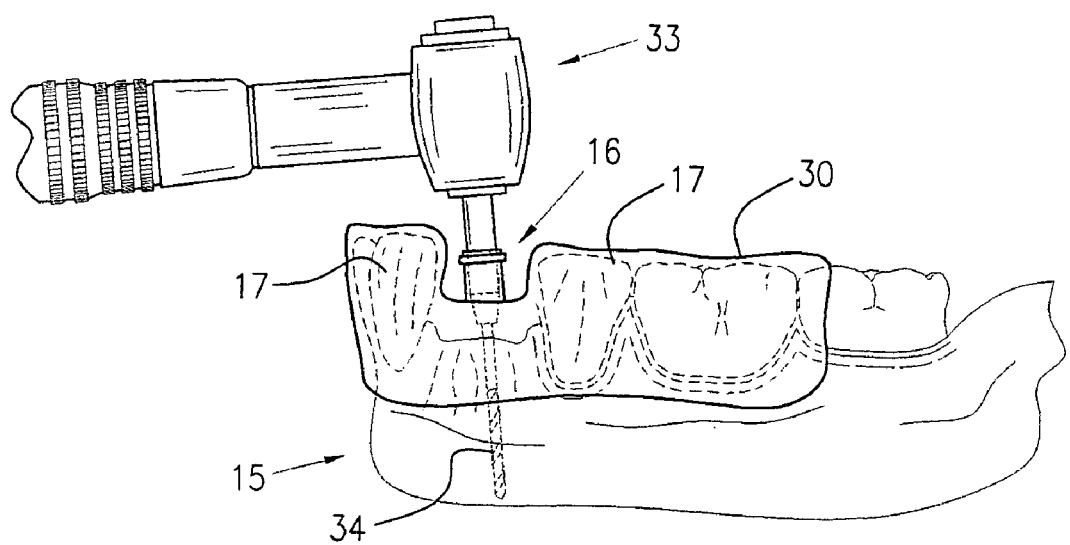
FIG. 11 is a side view depicting the preparation for placement of the implant of the present invention in a lower jaw.
Figure 12:
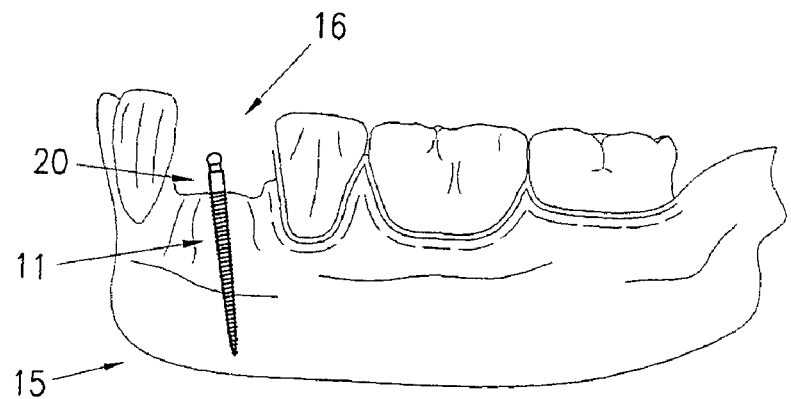
FIG. 12 is a side view depicting the implant of the present invention embedded in the lower jaw.

FIG. 11 is a side view of lower jaw 15 depicting the preparation for inserting implant 11 into bone material below the gum line of gap 16. After using a local anesthetic to desensitize the area, drill 33 with drill bit 34 is used to prepare a starter hole by positioning drill bit 34 through guide hole(s) 32 and drilling through the gum and about 4–8 mm into the underlying bone. By drilling through guide hole(s) 32, the operator and patient are assured that the starter hole is placed at the desired location and is drilled at the desired angle to ensure, as much as possible, that the starter is surrounded by bone material of equal mass on the buccal and lingual sides and on the mesial and distal sides respectively. Drill bit 34 has a smaller diameter than that of implants(s) 11. After preparing the starter holes, implant(s) 11 are threaded or screwed into the starter holes until carrier section 20 contacts the gum line of gap 16. Wrenches, ratchets and similar tools may be used to screw implant(s) 11 into the bone material. FIG. 12 depicts a side view of implant 11 after insertion into gap 16 in lower jaw 15.

Figure 13:
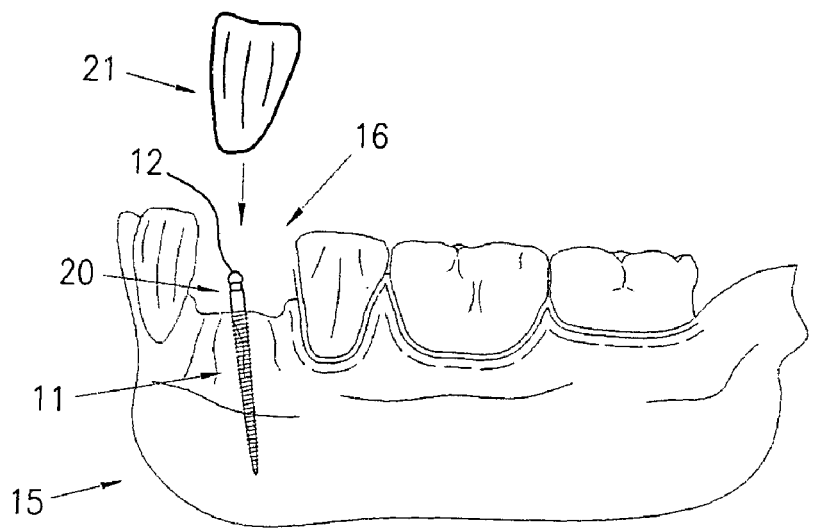
FIG. 13 depicts the attachment of a prosthetic tooth of the present invention to a dental implant; and, FIG. 14 is a bottom perspective view of two embodiments of prosthetic crowns of the present invention.

FIG. 13 depicts the view from FIG. 12 in which Crown 21 is placed on implant 11 after the attachment of implant 11 into lower jaw 15. As described above, tube 24 of crown 21 is filed with dental cement 26 and placed onto abutment end 12 of implant 11. Preferably, abutment end 12 is of such a size that it holds crown 21 in place without dental cement 26. However, in a more preferred embodiment, dental cement 26 is used to ensure a more durable fixed attachment. Preferably, the entire procedure from drilling the starter hole into a patient's gum tissue to fixedly attaching crown 21 onto implant 11 may be performed in one continuous process without the need for additional visits or months-long waiting periods before performing the next step in the installation procedure. Moreover, patient discomfort is reduced and a patient may eat normal food within hours after the completion of the operation.

Figure 14:
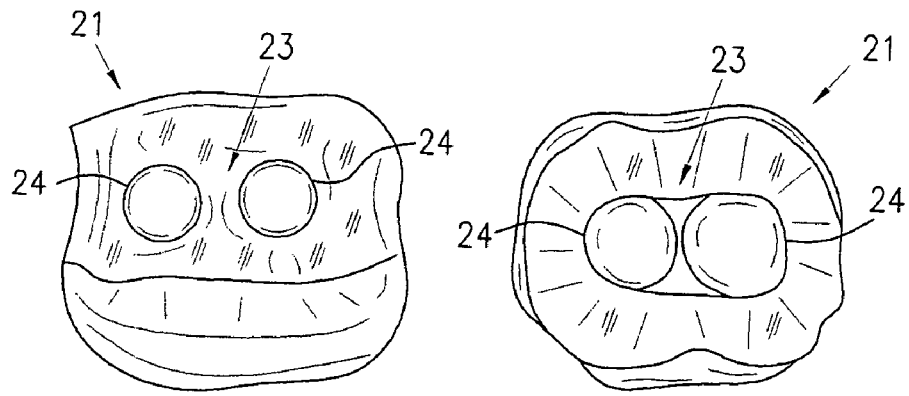

FIG. 14 is a bottom perspective showing crowns 21 fabricated from resin or porcelain fused metal. Clearly demonstrated are joining portion 23 and tube 24 extending from joining portion 23.

Thus it is seen that the objects of the invention are efficiently obtained, although changes and modifications to the invention should be readily apparent to those having ordinary skill in the art, which changes would not depart from the spirit and scope of the invention as claimed.

I claim:

1. A preformed prosthetic tooth replacement comprising:
a dental crown portion; and,
a joining portion including two bores, each of said two bores configured to fixedly receive an abutment end of an implant, each of said two bores having a diameter ranging in size from slightly greater than 1.6 mm to slightly greater than 2.5 mm and wherein said implant is integral, one-piece and has a first end a second end and a shaft;
wherein said first end is threaded and tapers to a point;
wherein said thread extends continuously along said shaft;
and wherein the diameter of said implant ranges from about 1.6 to about 2.5 mm.

2. In combination, a preformed prosthetic tooth and a dental implant, comprising:
a preformed prosthetic tooth, said preformed prosthetic tooth having a dental crown portion and a joining portion including a bore configured to fixedly receive an implant said bore having a diameter ranging in size from slightly greater than 1.6 mm to slightly greater than 2.5 mm; and,
an integral, one-piece dental implant, said at least one implant having a first end having a self-tapping thread and tapering to a point, a second end having an abutment end configured to be inserted into said bore of said preformed prosthetic tooth, and a shaft, the diameter of said implant ranging from about 1.6 to about 2.5 mm, said self-tapping thread extending continuously along said shaft from said abutment end to said point
wherein said implant may immediately receive said crown after implantation.

3. The combination preformed prosthetic tooth and dental implant recited in claim 2 wherein said abutment end further comprises a carrier section.

4. The combination preformed prosthetic tooth and dental implant recited in claim 2 wherein said abutment end has a generally spherical shape.

5. The combination preformed prosthetic tooth and dental implant recited in claim 2 wherein said abutment end has a polygonal shape.

6. The combination preformed prosthetic tooth and dental implant recited in claim 2 wherein said abutment end has a cone shape.

7. The combination preformed prosthetic tooth and dental implant recited in claim 2 wherein said abutment end has a combined polygonal and tapered shape.

8. The combination preformed prosthetic tooth and dental implant recited in claim 2, wherein said bore is configured to receive a generally spherical abutment end.

9. The combination preformed prosthetic tooth and dental implant recited in claim 2, wherein said bore is configured to receive a polygonal abutment end.

10. The combination preformed prosthetic tooth and dental implant recited in claim 2, wherein said dental crown portion is substantially formed in the shape of an incisor.

11. The combination preformed prosthetic tooth and dental implant recited in claim 2, wherein said dental crown portion is substantially formed into the shape of a bicuspid.

12. The combination preformed prosthetic tooth and dental implant recited in claim 2, wherein said dental crown portion is substantially formed into the shape of a cuspid.

13. The combination preformed prosthetic tooth and dental implant recited in claim 2, wherein said dental crown portion is substantially formed into the shape of a molar.

14. The combination preformed prosthetic tooth and dental implant recited in claim 2 wherein the diameter of said dental implant ranges from about 1.8 to about 2.2 mm.

15. In combination, a preformed prosthetic tooth and dental implant comprising:
a preformed prosthetic tooth, said preformed prosthetic tooth having a dental crown portion and a joining portion, said joining portion including two bores, each of said two bores configured to receive an implant; and,
two separate integral, one-piece dental implants, each of said two dental implants having a first end having a self-tapping thread and tapering to a point, a second end having an abutment end configured to be inserted into one of said bores of said preformed prosthetic tooth, and a shaft, the diameter of said implant ranging from about 1.6 to 2.5 mm, said self-tapping thread extending continuously along said shaft from said abutment end to said point
wherein said two separate implants may receive said prosthetic crown immediately after installation.

16. A method of attaching a prosthetic crown to a jawbone of a patient comprising:
placing an oral surgical guide stint over a target region of said jawbone;

drilling a starter hole having a diameter less than 1.6 mm and a depth of approximately 4–8 mm through an implant stint hole in said oral surgical guide stint and into said jawbone;

threading an integral, one-piece, self-tapping threaded dental implant having a diameter in the range of about 1.6 to 2.5 mm, a shaft, and an abutment end into said starter hole until a top of the abutment end is aligned with a tot of said implant stint hole and said abutment end protrudes above a gum line of said jawbone, wherein said threaded dental implant tapers to a point and said thread extends continuously along said shaft from said abutment end to said point; and, attaching a single prosthetic crown onto said abutment end without delay after said threading of said implant.

17. The method as recited in claim 13 wherein said threaded dental implant has a diameter ranging between about 1.8 to about 2.2 mm.

18. The method as recited in claim 13 wherein said further comprising drilling a second starter hole having a diameter of less than 1.6 mm and a depth of approximately 4–8 mm through a second implant stint hole in said oral surgical guide stint and into said jawbone;

threading a second integral, one-piece, self-tapping threaded dental implant having a diameter in the range of about 1.6 to 2.5 mm, a shaft, and an abutment end into said second starter hole until a top of the abutment end is aligned with a top of said implant stint hole and said abutment end protrudes above a gum line of said jawbone, wherein said threaded dental implant tapers to a point and said thread extends continuously along said shaft from said abutment end to said point; and, attaching a single prosthetic crown having two bore holes onto said abutment ends.

* * * * *

UNITED STATES PATENT AND TRADEMARK OFFICE
CERTIFICATE OF CORRECTION

| | | |
|---|---|---|
| PATENT NO. | : 7,108,511 B1 | Page 1 of 1 |
| APPLICATION NO. | : 10/641797 | |
| DATED | : September 19, 2007 | |
| INVENTOR(S) | : Todd E. Shatkin | |

It is certified that error appears in the above-identified patent and that said Letters Patent is hereby corrected as shown below:

(Column 9, line 9) - replace the word "tot" with the word --top--;

(Column 9, line 16) - replace the number "13" with the numbr --16--;

(Column 10, line 1) - replace the number "13" with the number --16--.

Signed and Sealed this

Fifteenth Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,108,511 B1 | Page 1 of 1 |
| APPLICATION NO. | : 10/641797 | |
| DATED | : September 19, 2006 | |
| INVENTOR(S) | : Todd E. Shatkin | |

It is certified that error appears in the above-identified patent and that said Letters Patent is hereby corrected as shown below:

(Column 9, line 9) - replace the word "tot" with the word --top--;

(Column 9, line 16) - replace the number "13" with the number --16--;

(Column 10, line 1) - replace the number "13" with the number --16--.

This certificate supersedes Certificate of Correction issued May 15, 2007.

Signed and Sealed this

Fifth Day of June, 2007

JON W. DUDAS
*Director of the United States Patent and Trademark Office*